United States Patent [19]
Kwon et al.

[11] Patent Number: 6,008,214
[45] Date of Patent: Dec. 28, 1999

[54] BICYCLIC COMPOUNDS

[75] Inventors: Chet Kwon, King of Prussia; William Henry Miller, Schwenksville, both of Pa.

[73] Assignee: SmithKline Beecham Corporation, Philadelphia, Pa.

[21] Appl. No.: 08/894,415

[22] PCT Filed: Aug. 22, 1995

[86] PCT No.: PCT/US95/10670

§ 371 Date: Feb. 18, 1997

§ 102(e) Date: Feb. 18, 1997

[87] PCT Pub. No.: WO96/06087

PCT Pub. Date: Feb. 29, 1996

Related U.S. Application Data

[63] Continuation of application No. 08/294,278, Aug. 22, 1994, abandoned.

[51] Int. Cl.$^6$ ..................... A61K 31/55; C07D 243/14; C07D 267/14; C07D 281/10
[52] U.S. Cl. ..................... 514/211; 514/213; 514/221; 540/490; 540/510; 540/512; 540/513; 540/523; 540/552; 540/573; 540/593
[58] Field of Search ..................... 540/513, 490, 540/552, 523, 593, 510, 573, 512; 514/221, 211, 213

[56] References Cited

U.S. PATENT DOCUMENTS 5,158,947 10/1992 Tatsuoka et al. ..................... 514/211
5,693,636 12/1997 Bondinell et al. ..................... 514/221

FOREIGN PATENT DOCUMENTS

94/14776 7/1994 WIPO .
97/24122 7/1997 WIPO .
97/24124 7/1997 WIPO .
98/15278 4/1998 WIPO .

*Primary Examiner*—Richard L. Raymond
*Assistant Examiner*—Ann M. Kessinger
*Attorney, Agent, or Firm*—Mary E. McCarthy; Stephen Venetianer; Charles M. Kinzig

[57] ABSTRACT

This invention relates to compounds of the formula:

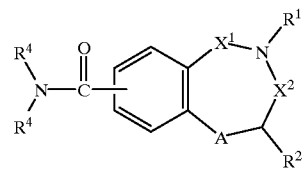

or a pharmaceutically acceptable salt thereof, which are effective for inhibiting platelet aggregation and bone resorption, pharmaceutical compositions for effecting such activity, and a method for using these compounds.

11 Claims, No Drawings

BICYCLIC COMPOUNDS

This application is a 371 of PCT/US95/10670 filed Aug. 22, 1995, which is a continuation of U.S. Ser. No. 08/294,278 filed Aug. 22, 1994, now abandoned.

FIELD OF THE INVENTION

This invention relates to pharmaceutically active bicyclic compounds, pharmaceutical compositions containing the compounds and methods of using the compounds. The instant compounds inhibit platelet aggregation. These compounds also inhibit the vitronectin receptor and are useful for the treatment of osteoporosis.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Also, recent studies have indicated that the attachment of osteoclasts to the bone matrix is mediated through cell surface adhesion receptors called integrins. For instance, Davies, et al., *J. Cell Biol.* 1989, 109, 1817, disclose that the osteoclast functional antigen, which is implicated in the regulation of bone resorption, is biochemically related to the vitronectin receptor. The vitronectin receptor, or the $\alpha_v\beta_3$ integrin, is known to bind to bone matrix proteins, such as osteopontin, bone sialoprotein and thrombospondin, which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat. EP 528 587 and 528 586 report substituted phenyl derivatives which inhibit osteoclast mediated bone resorption.

The present invention discloses novel bicyclic compounds, including benzazepines and benzodiazepines, which are inhibitors of the GPIIb-IIIa receptor and inhibit platelet aggregation. Also, the instant compounds are inhibitors of the vitronectin receptor. These agents inhibit bone resorption and are useful for the treatment of osteoporosis.

SUMMARY OF THE INVENTION

In one aspect this invention is a bicyclic compound comprising a substituted six-membered ring fused to a substituted seven-membered ring as described hereinafter in formula (I).

This invention is also a pharmaceutical composition which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

This invention is also a method of treating diseases which are mediated by ligands which bind to the vitronectin receptor. In a particular aspect, the compounds of this invention are useful for treating osteoporosis and diseases wherein bone resorption is a factor.

DETAILED DESCRIPTION OF THE INVENTION

This invention discloses bicyclic compounds which inhibit platelet aggregation and which inhibit bone resorption. The novel bicyclic compounds comprise a seven-membered ring fused to an aromatic six membered ring and having a nitrogen-containing substituent on the six membered ring and an aliphatic substituent containing an acidic moiety on the seven membered ring. The seven membered ring contains heteroatoms, such as nitrogen, oxygen and sulfur, and the six membered ring is carbocyclic.

The compounds of this invention are compounds of formula (I):

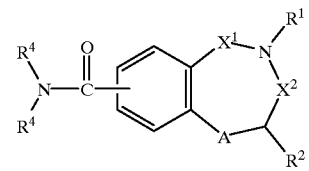

wherein:

A is NR', CHR', O or S;

$X^1$ and $X^2$ are C=O or $CH_2$, with the proviso that only one of $X^1$ or $X^2$ is C=O;

$R^1$ is H, $C_{1-6}$alkyl or $(CHR')_m$—Y;

$R^2$ is —$(CH_2)_t$—$CO_2R^3$;

$R^3$ is H, $C_{1-6}$alkyl or $(CHR')_m$—Ar;

$R^4$ and $R^{4'}$ independently are —$(CH_2)_s$—Ⓝ or —$(CH_2)_s$—NR'R'

Y is H, Ar, $C_{3-7}$cycloalkyl, $CO_2R^3$ or Tet;

R' is H, $C_{1-6}$alkyl or $(CH_2)_m$—Ar;

Ar is phenyl or naphthyl unsubstituted or substituted by one to three $C_{1-6}$alkyl, trifluoromethyl, halogen, OR', SR', CONR'$R^1$, $CO_2R^1$, $NO_2$ or $R^5R^1N$;

$R^5$ is H, $C_{1-6}$alkyl, $(CHR')_m$—Y or $CO(CHR')_m$—Y;

Ⓝ is pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydroazepine or hexahydroazepine;

m is 0 to 6;

s is 1 to 4; and t is 1 or 2;

or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. The meaning of any substituent at any one occurrence is independent of its meaning, or any other substituent's meaning, at any other occurrence, unless specified otherwise.

With reference to formula (I), suitably, $X^1$ is $CH_2$, $X^2$ is $C=O$ and A is NR'.

Preferably, with reference to formula (I), $X^1$ is $CH_2$, $X^2$ is $C=O$, A is NR', $R^1$ is $C_{1-4}$alkyl or $(CHR')_n$—Y, in which R' is H or $C_{1-4}$alkyl, m is 1 to 3 and Y is Ar or $C_{3-7}$cycloalkyl, and $R^4$ and $R^{4'}$ independently are —$(CH_2)_s$—Ⓝ, in which Ⓝ is piperidine, piperazine, pyridine, pyridinium or tetrahydropyridine and s is 1 to 3. Most preferably, Ⓝ is pyridine or piperidine.

Preferred compounds of this inventions are:

(±)-7-[[bis[2-(4-pyridinyl)ethyl]amino]carbonyl]-4-methyl-3-oxo-2,3,4,5-tetrahydro-1H-1,4-benzodiazepine-2-acetic acid, (±)-8-[[bis[2-(4-pyridinyl)ethyl]amino]carbonyl]-3-oxo-4-(2-phenylethyl)-2,3,4,5-tetrahydro-1H-1,4-benxodiazepine-2-acetic acid, (±)-7-[[bis[2-(4-piperidinyl)ethyl]amino]carbonyl]-4-methyl-3-oxo-2,3,4,5-tetrahydro-1H-1,4-benzodiazepine-2-acetic acid, and (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetic acid; or a pharmaceutically acceptable salt thereof.

The most preferred compounds of this invention are:

(±)-7-[[bis[2-(4-piperidinyl)ethyl]amino]carbonyl]-4-methyl-3-oxo-2,3,4,5-tetrahydro-1H-1,4-benzodiazepine-2-acetic acid, and (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetic acid; or a pharmaceutically acceptable salt thereof In the above description, $C_{1-4}$alkyl is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl, particularly cyclohexyl. Any combination of up to three substituents, such as chosen from $C_{1-6}$alkyl, trifluoromethyl, halogen, OR', SR', CONR'R$^1$, CO$_2$R$^1$, NO$_2$ or R$^5$R$^1$ N, on the cycloalkyl ring that is available by conventional chemical synthesis and is stable, is within the scope of this invention.

The accessible substituted seven-membered ring as referred of formula (I) is any saturated seven-membered ring which (i) contains up to two heteroatoms selected from the group of N, O and S, wherein S and N may optionally be oxidized, and (ii) is stable and may be synthesized by one skilled in the chemical arts in a form fused via two adjacent ring carbon atoms to a phenyl. Typical of accessible seven-membered rings are the common saturated rings of azepine, diazepine, thiazepin and oxazepin. Representative bicyclic rings formed by the combination of the accessible seven-membered and phenyl rings are: benazaepine, benzodiazepine, benzoxazepine, and benzothiazepine compounds. Benzodiazepine compounds are the preferred bicyclic compounds of the instant invention.

Certain radical groups are abbreviated herein. t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-6}$alkyl, Nph refers to 1- or 2-naphthyl and cHex refers to cyclohexyl. MeArg is $N^\alpha$-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to N-ethyl-N'(dimethylaminopropyl)-carbodiimide. HOBt refers to 1-hydroxybenzotriazole, THF refers to tetrahydrofuran, DMF refers to dimethyl formamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (II) with a compound of the formula (III):

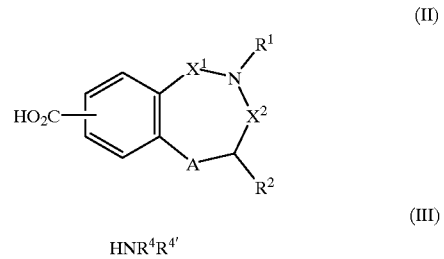

wherein $X^1$, $X^2$, $R^1$, $R^2$, A and $R^4$ and $R^{4'}$ are as defined in formula (I), with any reactive functional groups protected;

and thereafter removing the protecting groups, and optionally forming a pharmacetuically acceptable salt.

Compounds of Formula (II) are benzodiazepines, benzazepines, benzozepines, and benzothiazepines described in Bondinell, et al., PCT Publication No. WO 93/00095, (PCT/US92/05463) published Jan. 7, 1993. Reference should be made to such published patent application for its full disclosure, which is incorporated herein by reference.

Compounds of the formula (I) are prepared by the general methods described in Schemes I and II.

Scheme I

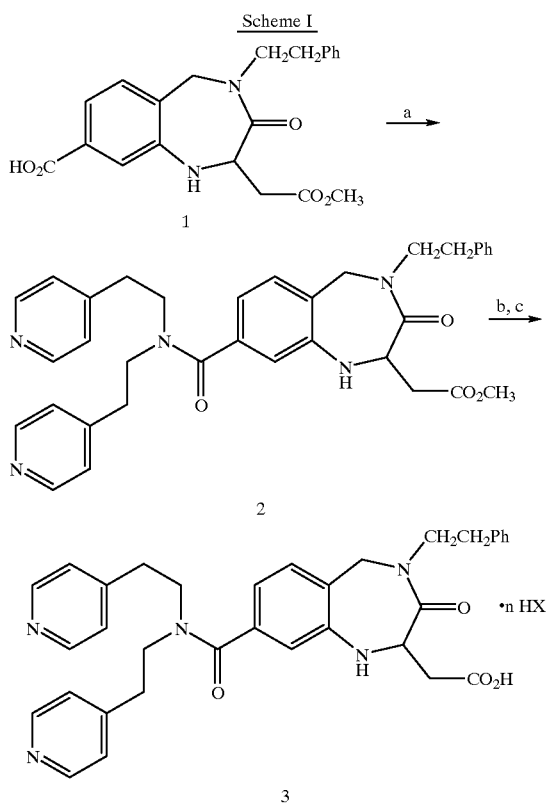

a) EDC, HOBT, (i-Pr)₂NEt, DMF, bis[2-(4-pyridyl)ethyl] amine; b) 1.0 N LiOH, aqueous THF; c) acidification.

Methyl (±)-8-carboxy-3-oxo4-(2-phenylethyl)-2,3,4,5-tetrahydro-1H-1,4-benzodiazepine-2-acetate (I-1), prepared as described by Bondinell, et al. (WO 93/00095), is converted to an activated form of the carboxylic acid using, for example, EDC and HOBT, or SOCl₂, and the activated form is subsequently reacted with an appropriate triamine, such as bis [2-(4-pyridyl)ethyl]amine, to afford the corresponding amide I-2. Many additional methods for converting a carboxylic acid into an amide are known, and can be found in standard reference books, such as "Compendium of Organic Synthetic Methods", Vol. I–VI (published by Wiley-Interscience). The methyl ester of I-2 is hydrolyzed using aqueous base, for example, aqueous LiOH in THF, or aqueous NaOH in methanol, and the intermediate carboxylate salt is acidified with a suitable acid, for instance TFA or HCl, to afford the carboxylic acid I-3. Alternatively, the intermediate carboxylate salt can be isolated, if desired.

Scheme II

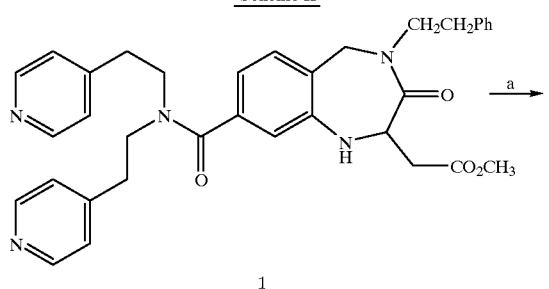

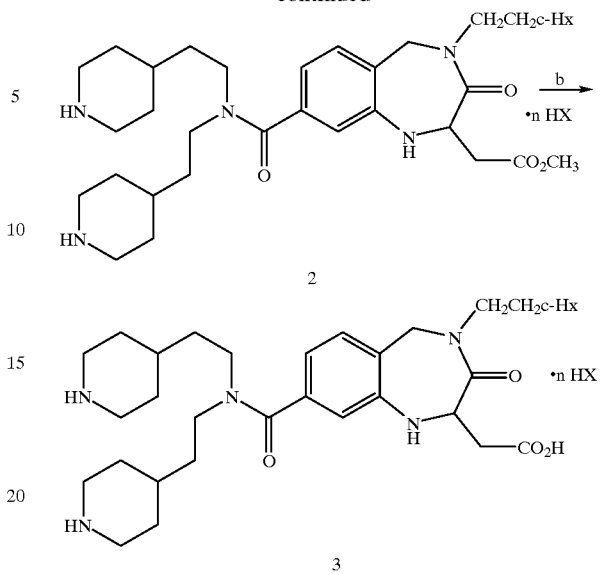

a) H₂, PtO₂, 1.0 N HCl, MeOH; b) see Scheme I.

Piperidine-containing compounds, such as II-3, can be prepared either from a suitably N-protected piperidine derivative, according to the methods described in Scheme 1, or from a pyridine precursor, such as II-1. For example, the pyridine subunits of II-1 can be reduced to the corresponding piperidine groups by hydrogenation over a suitable catalyst, preferably PtO₂, in the presence of acid, such as HCl. Under these conditions, other aromatic rings in the molecule, such as may be present in the substituent at the 4-position, may be reduced simultaneously. The resulting piperidinium salt II-2 is then converted to compound II-3 by the methods described in Scheme I.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide or peptide bonds is accomplished using conventional methods used to form amide bonds. Typically, the free amino group of a formula (III) HNR⁴R⁴ compound is coupled to an appropriate carboxylic acid substrate, such as a Scheme I, formula 1 compound, using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of, for example, a Scheme I, formula 1 compound, and subsequent reaction with the free amino group of a formula (III) HNR⁴R⁴ compound.

Acid addition salts of the compounds are prepared in a standard manner in a suitable solvent from the parent compound and an excess of an acid, such as hydrochloric, hydrobromic, sulfuric, phosphoric, acetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and $NH_4+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation and the treatment of sickle cell disease.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor and antiinflammatory agents, and be useful in the treatment of atherosclerosis and restenosis.

The compound is administered either orally or parenterally to the patient, in a manner such that the concentration of drug in the plasma is sufficient to inhibit platelet aggregation or bone resorption, or other such indication. The pharmaceutical composition containing the compound is administered at a dose between about 0.2 to about 50 mg/kg in a manner consistent with the condition of the patient. For acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 to 20 mg/kg. The compounds are administered one to four times daily at a level to achieve a total daily dose of about 0.4 to about 400 mg/kg/day. The precise level and method by which the compounds are administered is readily determined by one skilled in the arty by comparing the blood level of the agent to the concentration required to have a therapeutic effect.

This invention further provides a method for inhibiting the reocclusion of an artery or vein following fibrinolytic therapy, which comprises internal administration of a peptide of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or-indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The peptide is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The compounds may be tested in one of several biological assays to determine the concentration of compound which is required to have a given pharmacological effect.

Inhibition of RGD-mediated GPIIb-IIIa binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70C. until needed.

Competitive Binding to GPIIb-IIIa

The binding to the fibrinogen receptor (GPIIb-IIIa) was assayed by an indirect competitive binding method using $[^3H]$-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzadiazapines were added to the wells in quadruplicate. $[^3H]$-SK&F-107260 was applied to each well at a final concentration of 4.5 nM, followed by the addition of 1 $\mu$g of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 $\mu$M unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of $[^3H]$-SK&F-107260 by 50% at equilibrium). The IC50 is related to the equilibrium dissociation constant (Ki) of the antagonist based on the Cheng and Prusoff equation: $K_i = IC_{50}/(1+L/K_d)$, where L is the concentration of [3H]-SK&F-107260 used in the competitive binding assay (4.5 nM), and Kd is the dissociation constant of [3H]-SK&F-107260 which is 4.5 nM as determined by Scatchard analysis. The compounds of this invention inhibit [3H]-SK&F 107260 binding with Ki in the range of about 2 nM to about 1.0 µM. Preferred compounds generally have Ki of less than 60 nM.

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3 \times 10^5$ cells/ml. Peptides were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transmittance 5 min after addition of the agonist was used to calculate percent aggregation according to the formula % aggregation =[(90-CR)÷(90-10)]×100, where CR is the chart reading, 90 is the baseline, and 10 is the PRP blank reading. IC50's were determined by plotting [% inhibition of aggregation] vs. [concentration of peptide]. Peptides were assayed at 200 mM and diluted sequentially by a factor of 2 to establish a suitable dose response curve.

The compounds of this invention inhibit the aggregation of human platelets stimulated with ADP with IC50 of about 0.02 to about 2.0 µM. Preferred compounds have IC50 of less than 1 µM. The most preferred compounds have IC50 of less than 0.1 µM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

Inhibition of Vitronectin Binding

Solid-Phase [3H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 µg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 µM. This solution is then diluted to the required final compound concentration. Various concentrations of unlabeled antagonists (0.001–100 µM) were added to the wells in triplicates, followed by the addition of 5.0 nM of [3H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [3H]-SK&F-107260 was determined by liquid scintillation counting with the addition of 3 mL Ready Safe in a Beckman LS Liquid Scintillation Counter, with 40% efficiency. Nonspecific binding of [3H]-SK&F-107260 was determined in the presence of 2 µM SK&F-107260 and was consistently less than 1% of total radioligand input. The $IC_{50}$ (concentration of the antagonist to inhibit 50% binding of [3H]-SK&F-107260) was determined by a nonlinear, least squares curve-fitting routine, which was modified from the LUNDON-2 program. The $K_i$ (dissociation constant of the antagonist) was calculated according to the equation: $K_i = IC_{50}/(1+L/K_d)$, where L and $K_d$ were the concentration and the dissociation constant of [3H]-SK&F-107260, respectively.

Compounds of the present invention inhibit vitronectin binding to SK&F 107260 in the concentration range of about 15 to greater than 100 micromolar. Preferred compounds inhibit vitronectin binding at a concentration of less than 50 micromolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

The examples which follow are intended to in no way limit the scope of this invention, but are provided to illustrate how to make and use the compounds of this invention. Many other embodiments will be readily apparent and available to those skilled-in the art.

EXAMPLES

In the Examples, all temperatures are in degrees Centigrade. Mass spectra were performed using electro-spray (ES) ionization. Melting points were taken on a Thomas-Hoover capillary melting point apparatus and are uncorrected.

Celite® is filter aid composed of acid washed diatomaceous silica, and is a registered trademark of Mansville Corp., Denver, Colo. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support.

Methyl (±)-7-carboxy-4-methyl-3-oxo-2,3,4,5-tetrahydro-1H-1,4-benzodiazepine-2-acetate and methyl (±)-8-carboxy-3-oxo-4-(2-phenylethyl)-2,3,4,5-tetrahydro1H-1,4-benzodiazepine-2-acetate were prepared by the method of Bondinell, et al., WO 93/00095.

The following methods are illustrative of the manner of making certain useful intermediates for the preparation of the compounds of this invention.

Example 1

Preparation of (±)-7-[[bis[2-(4-pyridinyl)ethyl]amino]carbonyl]-4-methyl-3-oxo-2,3,4,5-tetrahydro-1H-1,4-benzodiazepine-2-acetic acid a) Bis [2-(4-pyridyl)ethyl]amine A mixture of 4-vinylpyridine (10.0 g, 95.1 mmole) and ammonium chloride (5.1 g, 95.1 mmole) in MeOH (90 mL) was heated to reflux under argon for 27 h. The resulting mixture was filtered and the filtrate was concentrated on the rotavap. The residue was dissolved in $H_2O$ (200 mL), and the solution was basified to pH 10.5 using 2 N NaOH. $CH_2Cl_2$ extraction (3×100 mL), drying ($MgSO_4$), and concentration gave a yellow oil (5.73 g, 49% crude). 2.9 g of this oil was chromatographed on silica gel (12% MeOH/$CH_2Cl_2$) to afford the title compound as a yellow oil (1.81 g, 16%). MS (ES) m/e 228 (M+H)$^+$.

b) Methyl (±)-7-[[bis[2-(4-pyridinyl)ethyl]amino]carbonyl]-4-methyl-3-oxo-2,3,4,5-tetrahydro-1H-1,4-benzodiazepine-2-acetate Diisopropylethylamine (0.35 g, 2.7 mmole) was added in one portion to a stirred mixture of bis [2-(4-pyridyl)ethyl]amine (0.37 g, 1.65 mmole), methyl (±)-7-carboxy-4-methyl-3-oxo-2,3,4,5-tetrahydro-1H-1,4-benzodiazepine-2-acetate (0.44 g, 1.50 mmole), EDC (0.34 g, 1.8 mmole), and HOBT . $H_2O$ (0.24 g, 1.8 mmole) in DMF (8 mL) at 0° C. under argon, and the reaction was allowed to warm to RT. After 19.5 h, the reaction was poured into a mixture of ice water (100 g) and 5% $NaHCO_3$ (10 mL) and extracted with $CH_2Cl_2$ (2×100 mL). The combined organic layers were washed with 5% $NaHCO_3$ (50 mL), dried ($MgSO_4$), and concentrated. Chromatography on silica gel (7% MeOH/CH2Cl$_2$) gave the title compound (0.7 g, 88%). MS (ES) m/e 502.4 (M+H)$^+$. c) (±)-7-[[Bis[2-(4-pyridinyl)ethyl]amino]carbonyl]-4-methyl-3-oxo-2,3,4,5-tetrahydro-1H-1,4-benzodiazepine-2-acetic acid 1.0 N LiOH (0.66 mL, 0.66 mmole) was added dropwise to a mixture of methyl (±)-7-[[bis[2-(4-pyridinyl)ethyl]amino]carbonyl]-4-methyl-3-oxo-2,3,4,5-tetrahydro-1H-1,4-benzodiazepine-2-acetate (0.16 g, 0.3 mmole) in THF (7 mL) and $H_2O$ (10 mL) at RT. After 22.5 h, the reaction mixture was concentrated on the rotavap. The resulting residue was neutralized with 1.0 N AcOH (1.5 mL) and kept in the refrigerator to give a crystalline product (0.114 g, 73%). Purification by ODS bond elute chromatography ($CH_3CN/H_2O$) afforded the title compound. MS (ES) m/e 488.2 (M+H)$^+$.

Example 2

Preparation of (±)-7-[[bis[2-(4-piperidinyl)ethyl]amino]carbonyl]-4-methyl-3-oxo-2,3,4.5-tetrahydro-1H-1,4-benzodiazepine-2-acetic acid a) Methyl (±)-7-[[bis[2-(4-piperidinyl)ethyl]amino]carbonyl]-4-methyl-3-oxo-2,3,4,5-tetrahydro-1H-1,4-benzodiazepine-2-acetate A mixture of methyl (±)-7-[[bis[2-(4-pyridinyl)ethyl]amino]carbonyl]-4-methyl-3-oxo-2,3,4,5-tetrahydro-1H-1,4-benzodiazepine-2-acetate (0.35 g, 0.65 mmole), $PtO_2$ (0.11 g, 0.48 mmole), 1.0 N HCI (1.3 mL, 1.3 mmole), and MeOH (30 mL) was hydrogenated at 45 psi in a Parr apparatus. After 5 h, the reaction mixture was filtered through celite® and concentrated to give the crude title compound (0.6 g) which was used without further purification. MS(ES) m/e 514.4 (M+H)$^+$.

b) (±)-7-[[Bis[2-(4-piperidinyl)ethyl]amino]carbonyl]-4-methyl-3-oxo-2,3,4,5-tetrahydro-1H-1,4-benzodiazepine-2-acetic acid Following the procedure of Example 1 (c), except substituting methyl (±)-7-[[bis[2-(4-piperidinyl)ethyl]amino]carbonyl]-4-methyl-3-oxo-2,3,4,5-tetrahydro-1H-1,4-benzodiazepine-2-acetate (0.32 g, 0.51 mmole) for methyl (±)-7-[[bis[2-(4-pyridinyl)ethyl]amino]carbonyl]-4-methyl-3-oxo-2,3,4,5-tetrahydro-1H-1,4-benzodiazepine-2-acetate, the title compound (0.41 g) was prepared. MS (ES) m/e 500.5 (M+H)$^+$.

Example 3

Preparation of (±)-8-[[bis[2-(4-pyridinyl)ethyl]amino]carbonyl]-3-oxo-4-(2-phenylethyl)-2,3,4,5-tetrahydro-1H-1,4-benzodiazepine-2-acetic acid a) Methyl (±)-8-[[bis[2-(4-pyridinyl)ethyl]amino]carbonyl]-3-oxo-4-(2-phenylethyl)-2,3,4,5-tetrahydro-1H-1,4-benzodiazepine-2-acetate Following the procedure of Example 1 (b), except substituting methyl (±)-8 -carboxy-3-oxo-4-(2-phenylethyl)-2,3,4,5 -tetrahydro-1H-1,4-benzodiazepine-2-acetate (0.57 g, 1.5 mmole) for methyl (±)-7-carboxy-4-methyl-3-oxo-2,3,4,5-tetrahydro-1H-1,4-benzodiazepine-2-acetate, the title compound (0.83 g, 93%) was prepared. MS (ES) m/e 592.4 (M+H)$^+$.

b) (±)-8-[[Bis[2-(4-pyridinyl)ethyl]amino]carbonyl]-3-oxo-4-(2-phenylethyl)-2,3,4,5-tetrahydro-1H-1,4-benzodiazepine-2-acetic acid Following the procedure of Example 1 (c), except substituting methyl (±)-8-[[bis[2-(4-pyridinyl)ethyl]amino]carbonyl]-3-oxo-4-(2-phenylethyl)-2,3,4,5-tetrahydro-1H-1,4-benzodiazepine-2-acetate (0.15 g, 0.25 mmole) for methyl (±)-7-[[bis[2-(4-pyridinyl)ethyl]amino]carbonyl]-4-methyl-3-oxo-2,3,4,5-tetrahydro-1H-1,4-benzodiazepine-2-acetate, the title compound (0.21 g) was prepared. MS (ES) m/e 578.2 (M+H)$^+$.

Example 4

Preparation of (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetic acid a) Methyl (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetate Following the procedure of Example 2(a), except substituting methyl (±)-8-[[bis[2-(4-pyridinyl)ethyl]amino]carbonyl]-3-oxo-4-(2-phenylethyl)-2,3,4,5-tetrahydro-1H-1,4-benzodiazepine-2-acetate (0.53 g, 0.90 mmole) for methyl (±)-7-[[bis[2-(4-pyridinyl)ethyl]amino]carbonyl]-4-methyl-3 -oxo-2,3,4,5-tetrahydro-1H-1,4-benzodiazepine-2-acetate, the title compound (0.63 g) was prepared. MS (ES) m/e 305.6 (M+2 H)$^{2+}$.

b) (±)-8-[[Bis[2-(4-piperidinyl)ethyl]amino]carbonyl]-4-(2-cyclohexylethyl)-3-oxo-2,3,4,5-tetrahydro-1H-1,4-benzodiazepine-2-acetic acid Following the procedure of Example 1 (c), except substituting methyl (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetate (0.26 g, 0.38 mmole) for methyl (±)-7-[[bis[2-(4-pyridinyl)ethyl]amino]carbonyl]-4-methyl-3-oxo-2,3,4,5-tetrahydro-1H- 1,4-benzodiazepine-2-acetate, the crude title compound was prepared. ODS chromatography (step gradient, 5–22% $CH_3CN/H_2O$ containing 0.1% TFA) afforded the title compound (0.25 g). MS (ES) m/e 596.4 (M+H)$^+$.

Example 5

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 6

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 7

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula:

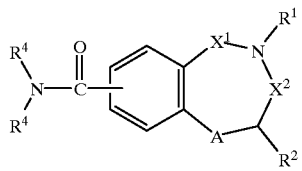

wherein:

A is NR', CHR', O or S;

$X^1$ and $X^2$ are C=O or $CH_2$, with the proviso that only one of $X^1$ or $X^2$ is C=O;

$R^1$ is H, $C_{1-6}$alkyl or $(CHR')_m$—Y;

$R^2$ is —$(CH_2)_t$—$CO_2R^3$;

$R^3$ is H, $C_{1-6}$alkyl or $(CHR')_m$—Ar;

$R^4$ and $R^{4'}$ independently are —$(CH_2)_s$—Ⓝ or —$(CH_2)_s$—NR'R';

Y is H, Ar, $C_{3-7}$cycloalkyl, $CO_2R^3$ or Tet;

R' is H, $C_{1-6}$alkyl or $(CH_2)_m$—Ar;

Ar is phenyl or naphthyl unsubstituted or substituted by one to three $C_{1-6}$alkyl, trifluoromethyl, halogen, OR', SR', CONR'$R^1$, $CO_2R^1$, $NO_2$ or $R^5R^1N$;

$R^5$ is H, $C_{1-6}$alkyl, $(CHR')_m$—Y or $CO(CHR')_m$—Y;

Ⓝ is piperidinyl or pyridinyl;

m is 0 to 6;

s is 1 to 4; and t is 1 or 2;

or a pharmaceutically acceptable salt thereof.

2. The compound according to claim 1 wherein $X^1$ is $CH_2$ and $X^2$ is C=O.

3. The compound according to claim 2 wherein A is NR'.

4. The compound according to claim 3 wherien $R^1$ is $C_{1-4}$alkyl or $(CHR')_m$—Y, in which R' is H or $C_{1-4}$alkyl, m is 1 to 3 and Y is Ar or $C_{3-7}$cycloalkyl.

5. The compound which is:

(±)-7-[[bis[2-(4-pyridinyl)ethyl]amino]carbonyl]-4-methyl-3-oxo-2,3,4,5-tetrahydro-1H-1,4-benzodiazepine-2-acetic acid or (±)-8-[[bis[2-(4-pyridinyl)ethyl]amino]carbonyl]-3-oxo-4-(2-phenylethyl)-2,3,4,5-tetrahydro 1H-1,4-benxodiazepine-2-acetic acid.

6. The compound which is:

(±)-7-[[bis[2-(4-piperidinyl)ethyl]amino]carbonyl]-4-methyl-3-oxo-2,3,4,5-tetrahydro-1H-1,4-benzodiazepine-2-acetic acid or (±)-8-[[bis[2-(4-piperidinyl)ethyl]amino]carbonyl]-4-(2-cyclohexylethyl)-3-oxo-2,3,4,5-tetrahydro-1H-1,4-benzodiazepine-2-acetic acid.

7. A pharmaceutical composition comprising a compound according to claim 1 and a pharmaceutically acceptable carrier.

8. A method for effecting inhibition of platelet aggregation which comprises administering to a mammal in need thereof an effective amount of a compound according to claim 1.

9. A method for treating stroke or a transient ischemia attack or myocardial infarction which comprises administering to a mammal in need thereof an effective amount of a compound according to claim 1.

10. A method for promoting reperfusion of an artery or vein and inhibiting reocclusion which comprises administering to a mammal in need thereof an effective amount of a fibrinolytic agent and a compound according to claim 1.

11. A method of inhibiting bone resorption in a mammal which comprises administering to a mammal in need thereof an effective amount of a compound according to claim 1.

* * * * *